(12) United States Patent
Liu et al.

(10) Patent No.: US 7,034,193 B2
(45) Date of Patent: *Apr. 25, 2006

(54) METHOD FOR PURIFYING SPENT ACID

(75) Inventors: Richard Wai-Chun Liu, Seabrook, TX (US); Philip Dean Hill, Baton Rouge, LA (US); Thomas Edwin Pruitt, Deer Park, TX (US); Forrest Lee Sanders, Katy, TX (US); Albert Yi Yang, Houston, TX (US)

(73) Assignee: Rhodia Inc., Cranbury, NJ (US)

( * ) Notice: Subject to any disclaimer, the term of this patent is extended or adjusted under 35 U.S.C. 154(b) by 9 days.

This patent is subject to a terminal disclaimer.

(21) Appl. No.: 10/826,052

(22) Filed: Apr. 15, 2004

(65) Prior Publication Data

US 2005/0010064 A1    Jan. 13, 2005

Related U.S. Application Data

(63) Continuation-in-part of application No. 10/418,193, filed on Apr. 17, 2003, now Pat. No. 6,818,799.

(60) Provisional application No. 60/486,229, filed on Jul. 10, 2003.

(51) Int. Cl.
*C07C 29/04* (2006.01)
*B01D 21/00* (2006.01)

(52) U.S. Cl. .................. 568/895; 568/899; 568/896; 568/913; 568/918; 568/383; 210/709; 210/703; 210/704; 210/708; 210/744; 210/196; 516/41

(58) Field of Classification Search ............... 568/895, 568/899, 896, 913, 918, 383; 210/709, 703, 210/704, 708, 744, 196; 516/41
See application file for complete search history.

(56) References Cited

U.S. PATENT DOCUMENTS

| | | | |
|---|---|---|---|
| 4,406,760 A | 9/1983 | Knudsen et al. | 204/130 |
| 5,156,745 A | 10/1992 | Cairo et al. | 210/703 |
| 6,197,837 B1 | 3/2001 | Hill et al. | 516/41 |
| 6,245,216 B1 | 6/2001 | Hill et al. | 208/13 |

*Primary Examiner*—Elvis O. Price

(57) ABSTRACT

A method for purifying a spent acid catalyst from an acid catalyzed chemical reaction that generates a mixture of a product, spent add and tar, includes the steps of separating the mixture of product, spent acid, and tar into a product fraction and a spent acid fraction, said spent acid fraction comprising a mixture of spent acid and tar, and separating the spent acid fraction, by flotation separation, centrifugation, or liquid-liquid coalescence, into a tar fraction and a de-tarred spent acid fraction. The fluidized tar and the de-tarred spent acid can each be further processed to produce concentrated acid.

20 Claims, 9 Drawing Sheets

Spent Acid before Cleaning
500X magnification @170°F

Spent Acid After Cleaning 500X magnification @170°F

Spent Acid before Cleaning 500X magnification @306°F

Spent Acid after Cleaning
500X magnification @306°F

Spent Acid before cleaning
500X magnification @ 320° F

Spent Acid after cleaning
500X magnification @ 320° F

METHOD FOR PURIFYING SPENT ACID

FIELD OF THE INVENTION

The present invention relates to a method for purifying a spent acid catalyst, more specifically, to a method for purifying a spent acid catalyst by removing tar, that is, acid-insoluble process by-products, from the spent acid catalyst.

BACKGROUND

Acids are used as catalysts in industrial hydrocarbon refining processes. For example, concentrated sulfuric acid is employed as a catalyst in industrial chemical reactions, such as indirect hydration reactions and esterification reactions. Such processes typically generate a mixture of a dilute form of acid that referred to in the industry as "spent acid" and tar. Such a mixture of spent acid and tar is corrosive, difficult to handle and difficult to reclaim, recycle, or dispose of.

It would be desirable to have a method for purifying the mixture of tar and spent acid to enable reclamation of the components of the mixture, to minimize fouling of the related process equipment, and to minimize the amount of wastes to be regenerated.

SUMMARY OF THE INVENTION

The present invention is directed to a method for purifying spent acid from an acid-catalyzed chemical reaction that generates a mixture of a product, spent add and tar, comprising separating the mixture of product, spent acid, and tar into a product fraction and a spent add fraction, said spent acid fraction comprising a mixture of spent acid and tar, and separating the spent acid fraction, by flotation separation, centrifugation, or liquid-liquid coalescence, into a tar fraction and a de-tarred spent acid fraction.

In one embodiment, the tar is fluidized and regenerated to produce fresh acid.

DETAILED DESCRIPTION OF THE INVENTION

Figure 1:
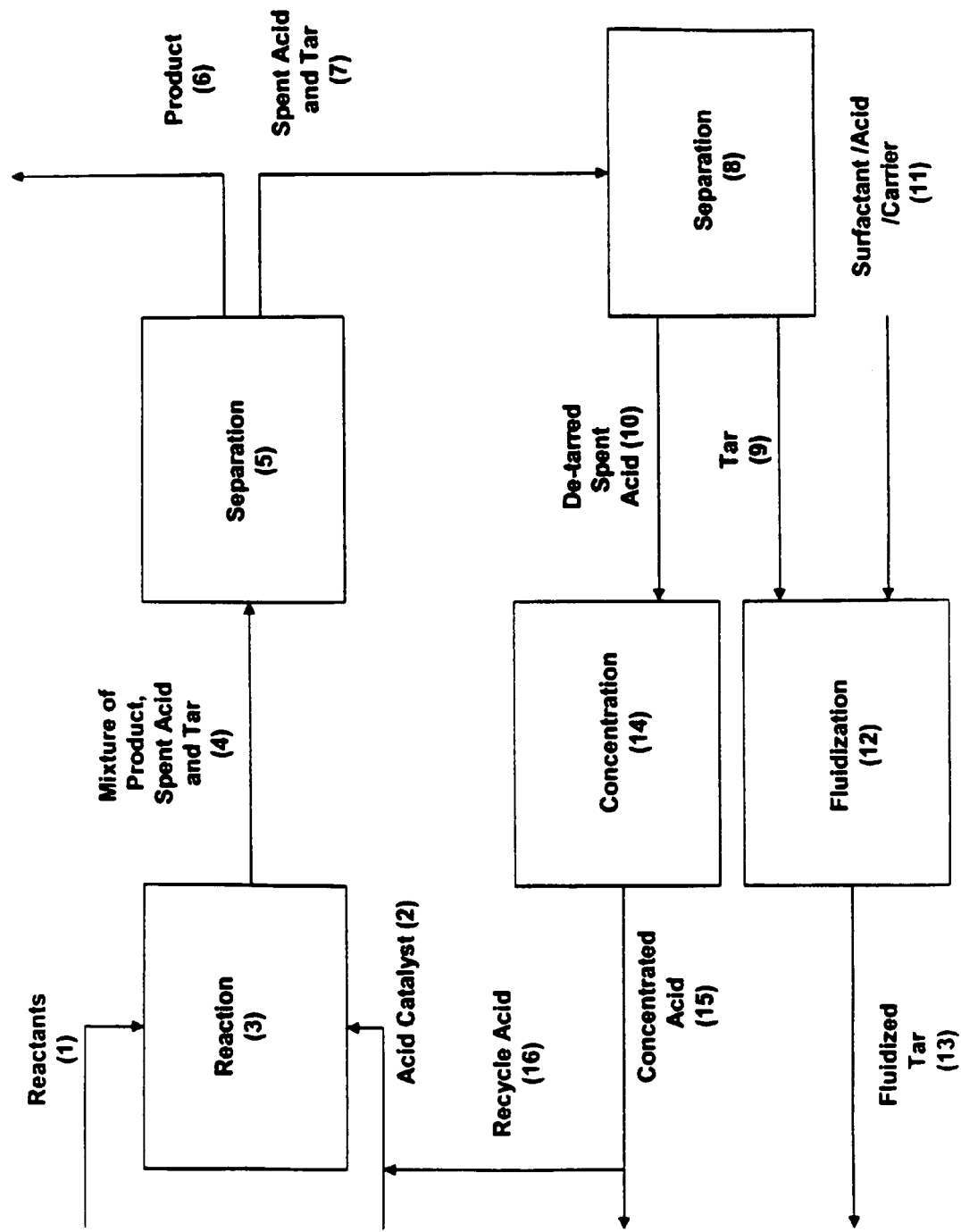
FIG. 1 is a schematic diagram for a method of purifying a spent acid catalyst according to the present invention.

Referring to FIG. 1, reactants (1) and an acid catalyst (2) are contacted and the reactants (1) undergo an acid catalyzed reaction (3) to generate a mixture of product, spent acid and tar (4).

The mixture (4) of product, spent acid and tar is separated (5) into product fraction (6) and a spent acid fraction (7). The separation (5) may be accomplished by know techniques, such as, for example, steam stripping. The product fraction (6) comprises a relatively higher amount of product than does spent acid fraction (7). The spent acid fraction (7) comprises a mixture of spent acid and tar. In one embodiment, the mixture of product, spent acid and tar is stripped to give an overhead fraction comprising a mixture of product, water and volatile by-products and a bottoms fraction comprising spent acid and tar. The product fraction (6) may be subjected to further processing. While the various material flows of the present method are each described in terms of a continuous process, a person skilled in the art will recognize that the method can be operated on a continuous, semi-continuous, or batch basis.

Suitable acid-catalyzed chemical reaction processes include, for example, acid-catalyzed indirect hydration processes, such as processes for making alkanols and acid-catalyzed esterification reactions.

In one embodiment, the acid catalyst (2) comprises sulfuric acid, more typically, concentrated sulfuric acid. As used herein, "concentrated sulfuric acid" means sulfuric acid having a concentration of greater than 65 percent by weight ("wt %"), more typically from about 65 wt % to about 99 wt % sulfuric acid.

In the manufacture of alkanols, an olefin is contacted with concentrated sulfuric acid catalyst to produce the corresponding sulfate ester. The ester is then hydrolyzed with water to form a mixture of alkanol product, spent sulfuric acid and tar. Suitable olefins include straight or branched ($C_2$–$C_6$)olefins, such as for example, ethylene, propene, butene, pentene, and hexene. Typical alkanol products include straight or branched ($C_2$–$C_6$)alkanols, such as ethanol, propanol, n-butanol, s-butanol, t-butanol, pentanol and hexanol.

For example, in the manufacture of isopropyl alcohol, propylene is contacted with concentrated sulfuric acid and water in sequence to form isopropyl alcohol and a dilute sulfuric acid, containing by-product tar, that is referred to as "spent acid". After the first reaction with concentrated sulfuric acid, propylene is converted to isopropyl sulfate esters. The sulfates are then reacted with water to form isopropyl alcohol. The water reaction is usually carried out by steam stripping the sulfates, which also functions to separate the isopropyl alcohol product in an overhead vapor stream. Numerous by-products can be formed, including tar, diisopropyl ether, acetone, propionaldehyde, and polymers of propylene and isopropyl alcohol. By-products can be present in the overhead vapor stream or in the stripper bottoms (liquid stream from stripper). The spent acid fraction typically comprises acid-soluble hydrocarbons and acid-insoluble mixed tars present in the stripper bottoms in the form of a dark dispersion. The spent acid has a brownish black coloration and is usually opaque. Sulfuric acid is present at dilute levels in the spent acid because water has been previously added for the hydration reaction.

In the manufacture of methyl ethyl ketone, butene is contacted with concentrated sulfuric acid and water, in sequence, to produce a mixture of s-butanol, spent add and tar and then stripped to produce an s-butanol product fraction and a mixture of spent acid and tar in a process closely analogous to the above-described process for making isopropyl alcohol. The s-butanol is then dehydrogenated to form the methyl ethyl ketone.

Certain esterification reactions are acid catalyzed. For example, an acrylamide or methacrylamide salt may be esterified with an alcohol in the presence of a sulfuric acid catalyst to produce an acrylic ester or a methacrylic ester. In the production of methyl methacrylate, methacrylamide sulfate is esterified with methanol in the presence of a concentrated sulfuric acid catalyst to form a mixture of methyl methcrylate, spent acid, tar and ammonia bisulfate. The methyl methacrylate product fraction is separated from the mixture of spent acid, tar and ammonia bisulfate.

Spent acid (7) comprises tar. As used herein, "tar" means a process by-product that is not soluble in the acid. Tar may comprise organic and inorganic components, such as acid-insoluble oils and suspended solids, and is typically visible as a brownish-black dispersed phase in spent acid (7). Once separated from the spent acid (7), tar is typically highly viscous and is very difficult to handle or transfer, for example, the tar is typically not pumpable. The spent acid fraction (7) is separated (8) into a tar fraction (9) and a de-tarred spent acid fraction (10). The tar fraction (9) comprises a relatively higher amount of tar than that present in the spent acid (7) or in the de-tarred acid fraction (10). The de-tarred fraction (10) comprises a relatively lower amount of tar than that present in spent acid (7). The separation (8) may be accomplished by a variety of techniques, including, for example, flotation separation, centrifugation, liquid-liquid coalescence.

In one embodiment, the spent acid fraction (7) is separated (8) into a tar fraction (9) and a de-tarred spent acid fraction (10) by flotation separation. In one flotation separation embodiment, gas bubbles are introduced into the spent acid fraction (7).

The gas bubbles may be formed from any gas that does not react or cause undesirable chemical byproduct reactions with the spent acid. Useful gases include nitrogen, carbon dioxide, argon, and air.

The gas may be introduced into the spent acid fraction (7) by any means known in the art, such as injection or by vacuum. One means for introducing the gas is an eductor, which employs the flow of spent acid fraction (7) therethrough to create a vacuum that draws gas into the spent acid. Another means for introducing the gas is blowing the gas through a gas sparger. The size of the bubbles introduced is typically about 3000 microns or less and most typically about 100 to about 300 microns in diameter. The bubbles are dispersed and allowed to contact the by-product tar for a time period sufficient for tar separation and formation of a tar layer on top of a layer of de-tarred spent acid. The separation can be carried out over a wide range of temperatures, e.g. typically up to about 350° F. and more typically about 100° F. to about 350° F. After the gas is introduced into the spent acid fraction (7), the resulting mixture of gas, spent acid, and tar may optionally be passed through a static or dynamic mixer to ensure a substantially homogeneous dispersion of bubbles therein.

As separation (8) progresses, an emulsified tar fraction (9) comprising gas bubbles and tar components, that is, oils and suspended solids, collects as froth on the surface of the spent acid fraction (7). After introduction of gas, the spent acid fraction (7) having the dispersed gas bubbles therein is allowed to settle to effect separation of the spent acid fraction (7) into a layer or phase of tar fraction (9) and a layer or phase of a cleaned, i.e., de-tarred, acid fraction (10). Typically, the gas-laden spent acid fraction (7) is conveyed to a tank or other container vessel and retained in such vessel for a time sufficient to allow phase separation to occur.

Flocculating agents or absorbent particles optionally may be employed in the present invention to assist in the removal of tar. Absorbent particles are particularly useful. Absorbent particles may be used in an amount and for a period of time sufficient to contact and absorb additional tar from the spent acid. Typically, the amount of absorbent particles used will be about 0.1 wt % or more, preferably about 0.25 weight percent (wt %) to about 5.0 wt %, more preferably about 0.50 wt % to about 3.0 wt %, and most preferably about 0.50 wt % to about 2.0 wt % based upon the weight of the spent acid fraction (7). Useful absorbent particles are carbon black and fumed silica. Carbon black is preferred. Preferred carbon blacks are industrially reinforcing carbon blacks and are activated. Useful carbon blacks have a nitrogen surface area/weight ratio of about 20 to about 700 $m^2$/gram, preferably about 70 to about 350 $m^2$/gram and most preferably about 80 to about 250 $m^2$/gram. Useful fumed silicas may have hydrophilic (Cab-0-SIL TS-720 by Cabot) or hydrophobic (Cab-0-SIL TS-720 by Cabot) or equivalent surfaces. Preferred surface area/weight ratios are about 100+/−20 $m^2$/gram. As needed, filtration and/or centrifugation may be used to separate tar-laden absorbent particles from spent acid and/or tar sludges.

Once present as separate layers, the tar fraction (9) can be captured or removed from the spent acid fraction (10) by any means known in the art, such as filtration, runoff/overflow trough or paddle action.

Examples of useful commercial flotation separation equipment include the Wemco Duperator 1+1 (Baker Hughes Process Systems), ISF-Induced Static Flotation Cell (Baker Hughes Process Systems) and Unicell Vertical IGF (Unicell Technologies).

In another embodiment, the spent acid fraction (7) is separated (8) into a tar fraction (9) and de-tarred spent acid fraction (10) by centrifugation. Centrifugation methods employ centrifugal force to separate the mixture of spent acid and tar into its components on the basis of density. In some centrifugation embodiments, a high velocity spiral flow of liquid is used to generate centripetal forces. In one centrifugation embodiment, a "hydrocyclone" comprises a tapered tube which extends along a flow direction from a wide end to a narrow end. The spent acid fraction (7) is introduced at the wide end of the tube through tangential inlets to provide a spiral flow that generates centripetal forces, which causes the denser components of spent acid fraction (7) to concentrate toward the tube wall, and the less dense components of spent acid fraction (7) to concentrate at the center of the tube. The denser components exit in the flow direction, while the less dense components form a reverse flow and exit opposite the flow direction. Suitable centrifugation equipment includes, for example, LAKOS® Liquid-Solids Separation Systems (Claude Laval Corporation, 1365 North Clovis Avenue, Fresno, Calif., U.S.A. 93727, Baker Process Vortoil hydrocyclones (Baker Hughes,)

In another embodiment, the spent acid fraction (7) is separated (8) into a tar fraction (9) and de-tarred spent acid fraction (10) by liquid-liquid coalescence. A liquid-liquid coalescer is a device for separating a mixture of immiscible liquids, wherein the mixture comprises a discontinuous liquid phase that is dispersed in a continuous liquid phase, by contacted with a coalescing medium to cause the dispersed phase to merge into larger droplets which then separate from the continuous phase on the basis of density. Suitable coalescing media include a knitted mesh of, e.g., stainless steel wool. Suitable liquid-liquid coalescence equipment includes, for example, (ACS Industries, LP, Separations Technology Division).

The de-tarred spent acid fraction (10) may, optionally, be concentrated (14) by known techniques, such as, for example, distillation, to provide concentrated acid (15). The concentrated acid (15) may then be recycled (16) as acid catalyst (2) in the acid-catalyzed chemical reaction (3) or put to another use. The treatment method of the present invention reduces fouling of process equipment, for example, heat exchangers, storage tanks, used in the concentration (14) of de-tarred spent acid (10), compared to analogous methods wherein the tar is not separated from the spent acid prior to concentration of the spent acid.

Tars, such as those of tar fraction (9), are typically highly viscous and intractable. In one embodiment of the present invention, the tar fraction (9) is fluidized (12) to generate fluidized tar (13), which has a lower viscosity than and is more easily handled than the tar fraction (9). Fluidized tar (13) is more flowable and pumpable and thus much easier to transport and handle than tar fraction (9).

In one embodiment, the tar fraction (9) is fluidized by adding a carrier, such as, for example, acid such as sulfuric acid, diesel fuel, or other organic solvent, such as, for example, xylene, to the tar fraction (9) and mixing the tar fraction (9) and carrier by, for example, mechanical agitation or recirculation, to produce the fluidized tar (13).

In another embodiment, the tar fraction (9) is fluidized according to one of the methods set forth in U.S. Pat. Nos. 6,197,837 and 6,245,216, the respective disclosures of which are each hereby incorporated herein by reference, to produce the fluidized tar (13). As described in those patents, tar having an organic acid content of greater than about 20% may be fluidized by adding a surfactant to the tar.

Suitable surfactants (11) are those that are compatible with an acid environment and may be selected from nonionic surfactants, cationic surfactants, anionic surfactants, and amphoteric surfactants, more typically nonionic surfactants, cationic surfactants, and anionic surfactants. Selection of an appropriate surfactant or surfactant mixture is made based on the composition of the tar to be fluidized and an experimentally tested for compatibility with the tar and stability of fluidized mixtures of the tar and surfactant.

Suitable nonionic surfactants are those having a hydrophilic lipophilic balance ("HLB") of from about 8 to about 16, more typically from about 10 to about 12.5, and include, for examples, condensates comprising from about 2 to about 9 moles of alkylene oxide, such as ethylene oxide, per mole of a hydrophobic moiety such as a ($C_8$–$C_{24}$) aliphatic primary or secondary alcohol or a ($C_6$–$C_{12}$) alkyl phenol, as well as mixtures of such surfactants.

Suitable cationic surfactants are those having an HLB of at least 10 and include, for example, imidazolines, dialkyl quaternary compounds, alkoxylated fatty amines, aliphatic or aromatic fatty amines, aliphatic fatty amides, or quarternary ammonium derivatives, as well as mixtures of such surfactants.

Suitable anionic surfactants are those having an HLB of at least 10 and include, for example, salts of alkyl benzene sulfonates, alkyl sulfates, alkyl ether sulfates, alkaryl ether sulfates, dialkyl sulfosuccinates polyalkoxylated alcohol sulfates, and ether phosphates, as well as mixtures of such surfactants. In one embodiment, the surfactant is a linear isopropylamine dodecylbenzene sulfonate.

Suitable amphoteric surfactants are those having an HLB of at least 10 and include, for example, alkali salts of amphocarboxyglycinates and amphocarboxypropionates, alkyl amphodipropionates, alkyl amphodiacetates, alkyl amphopropyl sulfonates, as well as mixtures of such surfactants. In one embodiment, the cationic surfactant comprises a cocoamphodipropionate.

In one embodiment, which may be appropriate in cases wherein the tar fraction (9) has an acid content of greater than about 20%, more typically greater than about 50%, the tar is fluidized by adding a surfactant (11), typically in an amount of from about 0.2 wt % to about 7.5 wt % based on the total weight of fluidized tar, to the tar stream (9) and mixing the tar and surfactant (11) to form a fluidized tar, without introducing any additional acid to the tar fraction (9). Optionally, a carrier other than sulfuric acid, such as, for example, water, diesel fuel, or other organic solvent such as xylene, may also be added to the tar fraction (9), in addition to the surfactant. The carrier may be added separately or as a mixture with the surfactant. In each case, suitable mixing may be accomplished by, for example, mechanical agitation or by recirculation.

In another embodiment, the tar fraction (9) is fluidized by adding a surfactant (11) and sulfuric acid, in an amount sufficient to provide acid content in the tar of greater than or equal to 20 wt %, more typically greater than or equal to 50 wt %, to the tar fraction (9). The acid and surfactant (11) may be added separately or as a mixture. In one embodiment, sulfuric acid of about 75% to about 98% concentration and at a temperature of about 60° F. to 150° F. is introduced to the tar with mixing and then a surfactant, typically in an amount of from about 0.2 wt % to about 7.5 wt % based on the total weight of fluidized tar (13), is added to the mixture of tar and acid, with continued mixing. In another embodiment the acid and surfactant are mixed prior to addition to the tar fraction (9) and a mixture (11) of acid and surfactant is added to the tar fraction (9). Optionally, an additional carrier, such as, for example, water, diesel fuel, or other organic solvent such as xylene may also be added to the mixture of tar, acid and surfactant. The carrier may be added separately or as a mixture with the acid or the surfactant. In each case, suitable mixing may be accomplished by, for example, mechanical agitation or by recirculation.

The fluidized tar (13) may be disposed of without further processing, or, more typically, be subjected to further treatment to reclaim sulfur values from the fluidized tar (13).

Figure 2:
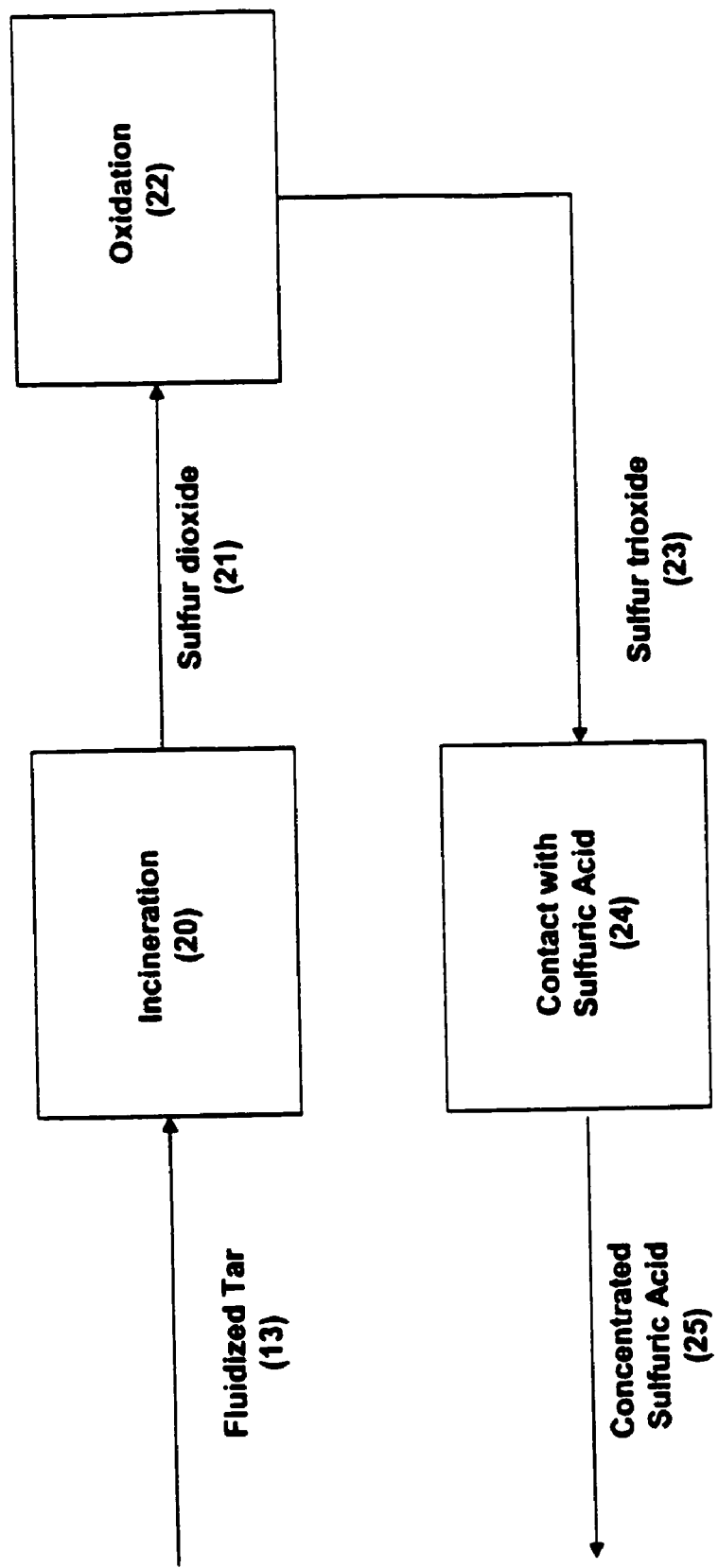
FIG. 2 is a schematic diagram for a method of reclaiming sulfur values from a fluidized tar.

Referring now to FIG. 2, in order to reclaim sulfur values from the fluidized tar (13), the fluidized tar (13) is incinerated (20) to produce sulfur dioxide (21). In one embodiment, the sulfur dioxide (21) is then oxidized (22) to sulfur trioxide (23) by, for example, contacting the sulfur dioxide with oxygen in the presence of a suitable oxidation catalyst, such as, for example, vanadium pentoxide. Alternatively, the sulfur dioxide (21) may be put to another use. In one, embodiment, the sulfur trioxide (23) is contacted with sulfuric acid to produce concentrated sulfuric acid (25). Alternatively, the sulfur trioxide (23) may be put to other use. In one embodiment, the concentrated sulfuric acid (25) is returned to the acid-catalyzed chemical reaction process as the acid catalyst (2). Alternatively, the concentrated sulfuric acid (25) may be put to another use.

EXAMPLE 1

Figure 3:
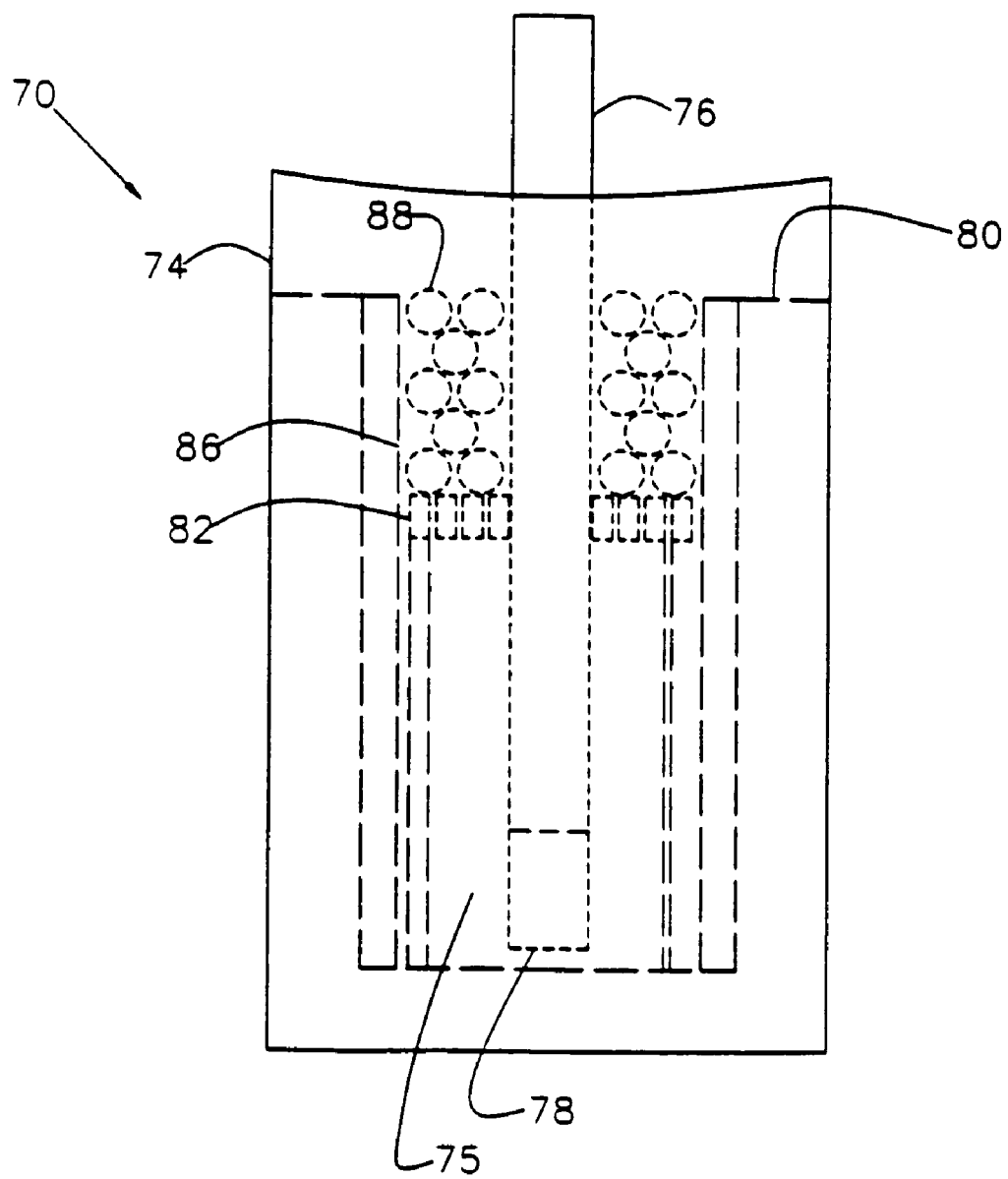
FIG. 3 is a longitudinal cross-sectional view of a flotation separation apparatus.

The procedure of Example 1 was conducted using the separation apparatus (70) shown in FIG. 3. A glass jar (74) was equipped with:

a glass column (75), a glass tube (76) and sparger (78) having 20–50 micron holes, a filter paper, which was doughnut-shaped, made of glass fiber (80), and supported between the column (76) and the inner wall of the jar (74), a perforated plate (82), which was doughnut-shaped, made of polytetrafluoroethylene (Teflon™), and supported inside column (75), and a plurality of glass beads (88) supported on plate (82).

A mixture of spent acid and tar (140° F. to 170° F.) was introduced into glass jar (74) up to a level of the filter paper (80). Microscopic bubbles of nitrogen gas (at a flow rate of 2 cubic feet per hour) were introduced into the mixture through the tube (76) and gas sparger (78). Tar floated up column (75), around and over spheres (88), and collected on top of the filter paper (80). A sample of the tar was found to have a viscosity of over 10,000 centipoise (Brookfield viscometer at 77° F.).

Samples of spent acid were collected from the annular space between column (75) and the wall of the jar (74) at the initiation of gas flow and at 6 minutes after initiation of gas flow. The samples of spent acid were analyzed to determine their acid content, water content and carbon content. Acid content was determined by titration, water content was determined potentiometrically using a 701 KF Titrino tester (Brinkmann), and carbon content was determined tested using a Leco CHN (carbon, hydrogen and nitrogen) instrument. Results are set forth below in Table 1, as percent by weight (wt %) at the initiation of gas flow (t=0) and after 6 minutes of gas flow (t=6 minutes).

TABLE 1

| Sample/Time | Acid Content (wt %) | Water Content (wt %) | Carbon Content (wt %) |
|---|---|---|---|
| Spent Acid Fraction/ t = 0 | 48.1 | 51.9 | 0.56 |
| De-tarred Spent Acid/ t = 6 minutes | 48.2 | 51.4 | 0.20 |

The amount of carbon remaining in the spent acid after 6 minutes of treatment was significantly less than that in the spent acid fraction prior to treatment.

Figure 4:
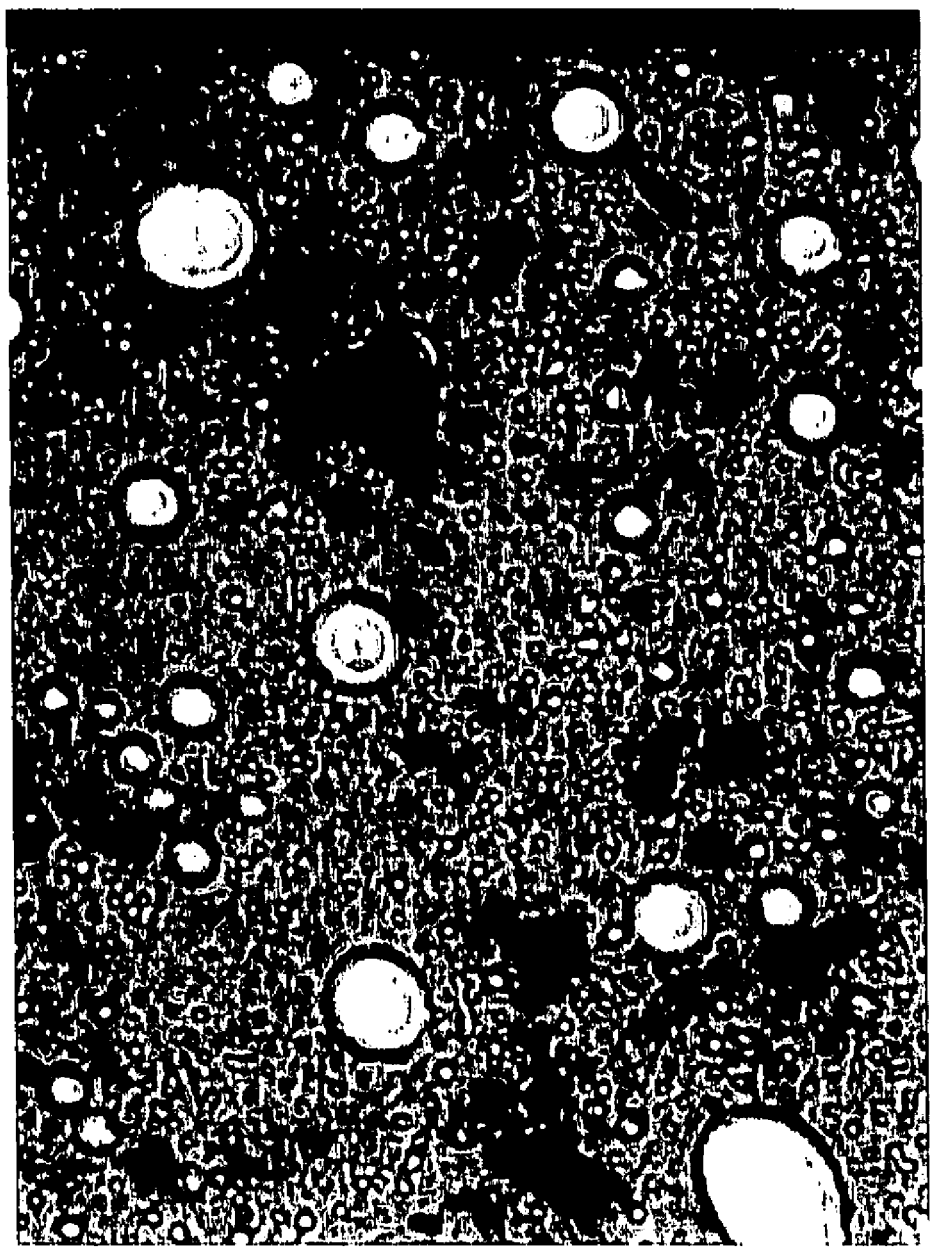
FIG. 4 is a micrograph (500× magnification) of the mixture of spent acid and tar referred to in Example 1.
Figure 5:
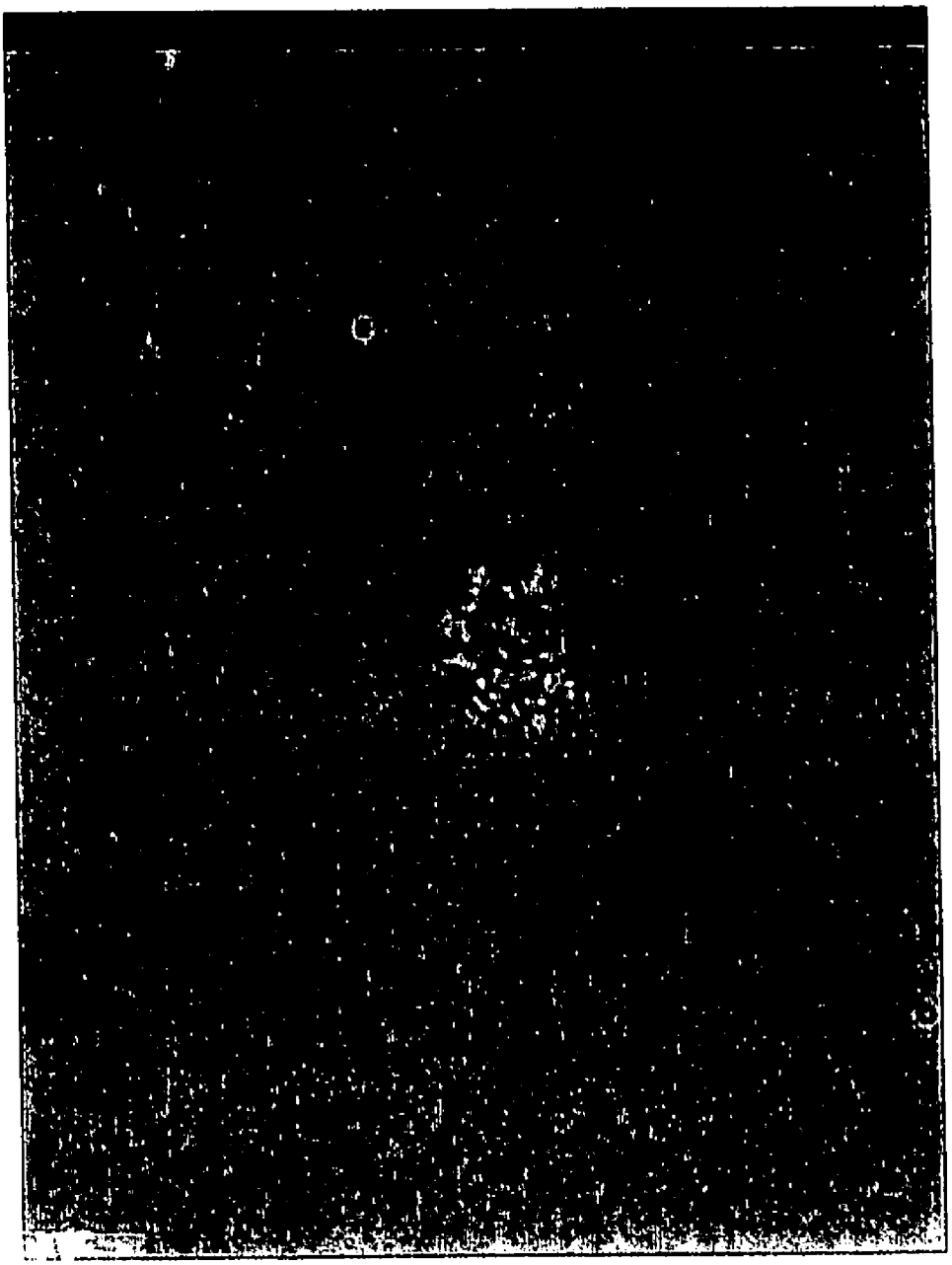
FIG. 5 is a micrograph (500× magnification) of the spent acid produced by separation of the mixture of tar and spent acid shown in FIG. 4.

A micrograph of a sample of the mixture of spent acid and tar (at t=0) is shown in FIG. 4 and a micrograph of a sample of the de-tarred spent acid (at=6 minutes) is shown in FIG. 5. Each of the micrographs is shown at 500× magnification. The mixture spent acid and tar exhibited more visible tar dispersion and a higher turbidity than the de-tarred spent acid.

EXAMPLE 2

The procedure of Example 2 was conducted in separation apparatus (70) in substantially the same manner as the procedure of Example 1, except that a different operating temperature was used.

The separation apparatus (70) was preheated to 306° F. In a separate jar, also heated to 306° F., spent acid and a small amount of tar were mixed together rapidly and then added to jar (74). A loose layer of tar was noticed to form rapidly on the surface.

A sample was collected at the tar layer and at the bottom of jar (74) at the initiation of gas flow. De-tarred acid samples were also collected near the bottom of apparatus (74) at 2 and at 5 minutes after initiation of gas flow. The carbon, acid, and water content of each of the samples were determined according to the methods described above in Example 1. Results are set forth below in Table 2, as percent by weight (wt %) at the initiation of gas flow (t=0), after 2 minutes of gas flow (t=2 minutes), and after 5 minutes of gas flow (t=5 minutes).

TABLE 2

| Sample/Time | Acid Content (wt %) | Water Content (wt %) | Carbon Content (wt %) |
|---|---|---|---|
| Top layer/ t = 0 | 60.1 | 38.6 | 1.04 |
| Bottom Layer/ t = 0 | 61.1 | 38.4 | 0.27 |
| Bottom Layer/ t = 2 minutes | 61.7 | 37.9 | 0.28 |
| Bottom Layer/ t = 5 minutes | 61.5 | 38.1 | 0.19 |

The initial top tar layer sample had the highest tar content, even before the nitrogen sparging was started. The sample of bottom layer taken a t=0 was down to 0.27% carbon before sparging was started. The carbon content of the bottom layer was unchanged after 2 minutes of sparging, but was reduced to 0.19% after 5 minutes of sparging.

Figure 6:
FIG. 6 is a micrograph (500× magnification) of the mixture of spent acid and tar referred to in Example 2.
Figure 7:
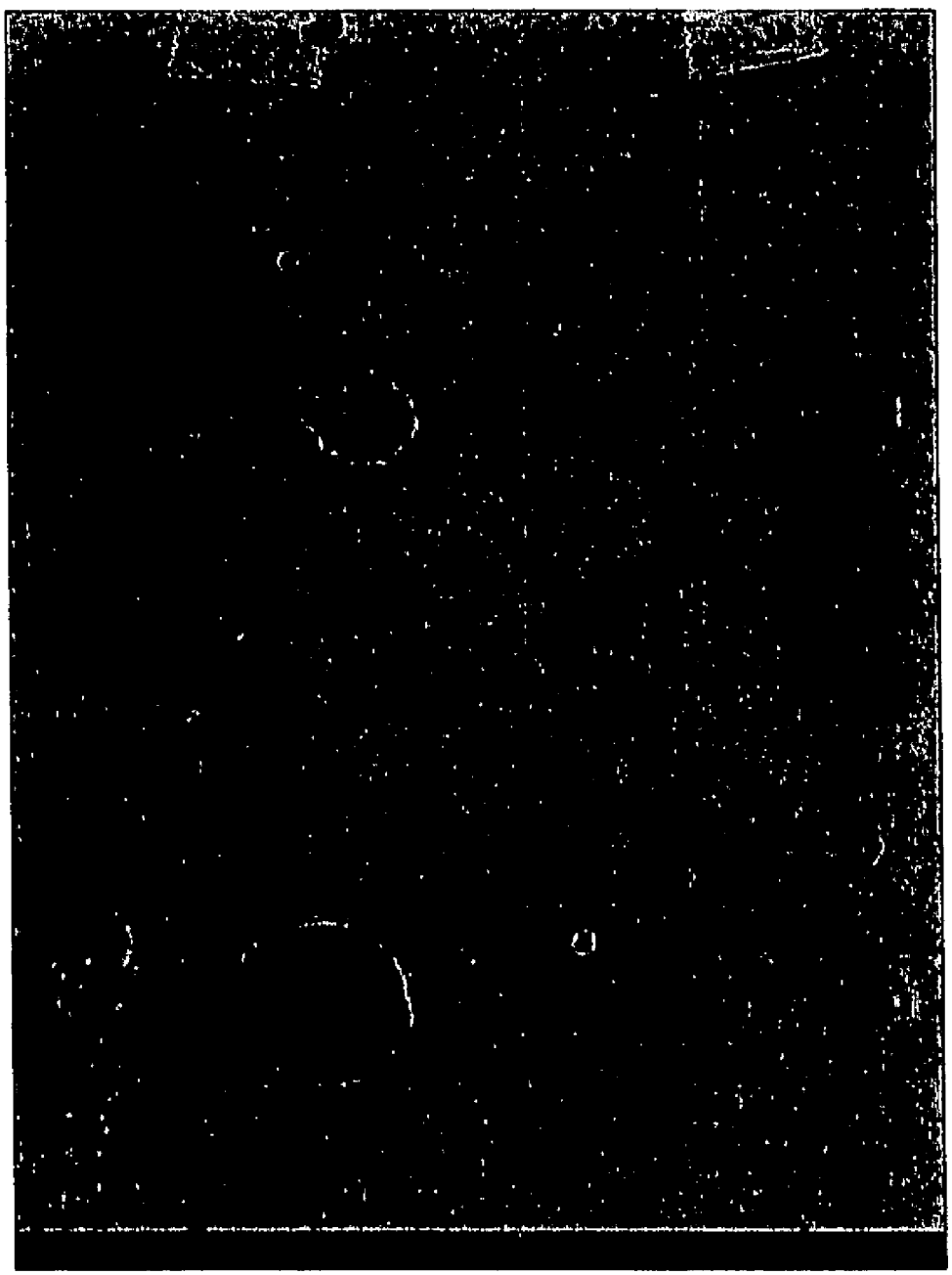
FIG. 7 is a micrograph (500× magnification) of the spent acid produced by separation of the mixture of tar and spent acid shown in FIG. 6.

A micrograph of a sample of the mixture of spent acid and tar (top layer, at t=0) is shown in FIG. 6 and a micrograph of a sample of the de-tarred spent acid (bottom layer, at t=5 minutes) is shown in FIG. 7. Each of the micrographs is shown at 500× magnification. The mixture of spent acid and tar exhibited more visible tar dispersion than the de-tarred spent acid.

EXAMPLE 3

The procedure of Example 3 was conducted in a separation apparatus made by removing the plate (82) and spheres (88) from the separation apparatus (70). The apparatus was preheated to 320° F. and warm spent acid fraction (130° F.) was poured into the jar (74). The spent acid fraction was heated to 320° F. under constant stirring. Once the target temperature was reached, nitrogen gas was introduced through tube (76) and glass sparger (78) into the bottom of the jar (74) at about 2 cubic feet/minute. Samples of spent acid were collected from the bottom of jar (74) at the initiation of gas flow, 5 minutes after initiation of gas flow, and 10 minutes after initiation of gas flow. The carbon content of each of the samples was determined according to the method described above in Example 1. Results are set forth below in Table 3, as percent by weight (wt %) at the initiation of gas flow (t=0), 5 minutes after initiation of gas flow (t=5 minutes), and 10 minutes after initiation of gas flow (t=10 minutes).

TABLE 3

| Sample/Time | Carbon Content (wt %) |
|---|---|
| Spent Acid/ t = 0 | 0.5 |

TABLE 3-continued

| Sample/Time | Carbon Content (wt %) |
|---|---|
| Spent Acid/ t = 5 minutes | 0.35 |
| Spent Acid/ t = 10 minutes | 0.32 |

The initial (t = 0) sample of spent acid exhibited the highest carbon content, whereas the carbon contents of samples of spent acid taken at 5 minutes and at 10 minutes were progressively lower.

Figure 8:
FIG. 8 is a micrograph (500× magnification) of the mixture of spent acid and tar referred to in Example 3.
Figure 9:
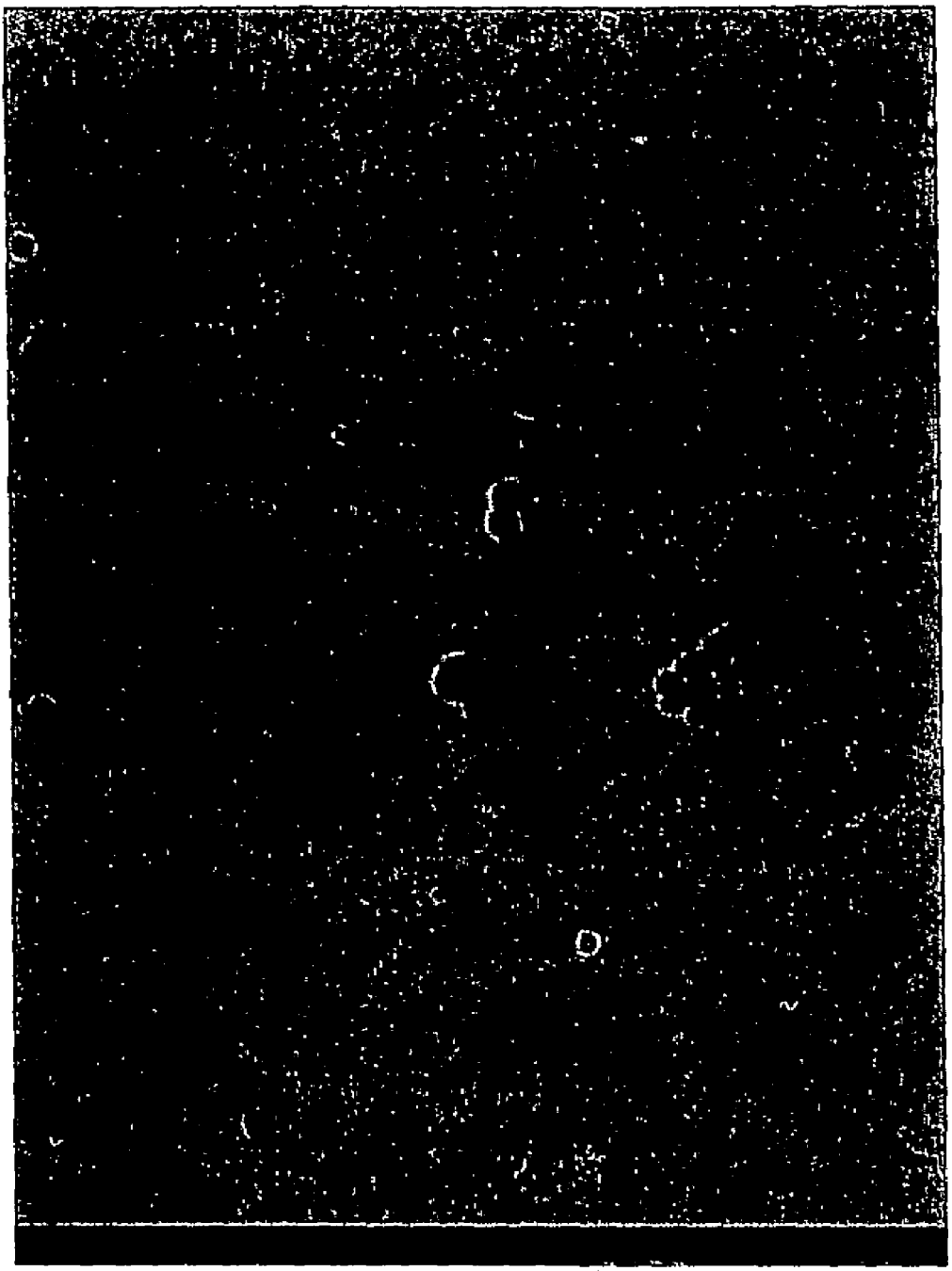
FIG. 9 is a micrograph (500× magnification) of the spent acid produced by separation of the mixture of tar and spent acid shown in FIG. 8.

A micrograph of the mixture of spent acid and tar (at t=0) is shown in FIG. 8 and micrograph of the de-tarred spent acid (at t=10) is shown in FIG. 9. Each of the micrographs is shown at 500× magnification. The mixture of spent acid and tar exhibited more visible tar dispersion than the de-tarred spent acid It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. A method for purifying spent acid from an acid-catalyzed chemical reaction that generates a mixture of a product, spent add and tar, comprising separating the mixture of product, spent add, and tar into a product fraction and a spent add fraction, said spent acid fraction comprising a mixture of spent acid and tar, and separating the spent acid fraction, by flotation separation, centrifugation, or liquid-liquid coalescence, into a tar fraction and a de-tarred spent acid fraction.

2. The method of claim 1, wherein the acid catalyzed chemical reaction comprises hydrating an olefin with water in the presence of a sulfuric acid catalyst and the product comprises an alkanol.

3. The process of claim 2, wherein the olefin comprises propylene and the product comprises isopropanol.

4. The process of claim 2, wherein the olefin comprises butene and the product comprises s-butanol.

5. The process of claim 4, further comprising dehydrogenating the s-butanol to form methyl ethyl ketone.

6. The method of claim 1, wherein the acid catalyzed chemical reaction comprises esterifying an acrylamide or methacrylamide salt with an alcohol in the presence of a sulfuric acid catalyst and the product comprises an acrylic ester or a methacrylic ester.

7. The process of claim 6, wherein the acrylamide or methacrylamide salt comprises methacrylamide sulfate, the alcohol comprises methanol, and the product comprises methyl acrylate or methyl methacylate.

8. The method of claim 1, wherein the mixture of product, spent acid, and tar is separated into a product fraction and a spent acid fraction by steam stripping.

9. The method of claim 1, wherein the spent acid fraction is separated into a tar fraction and a de-tarred spent acid fraction by flotation.

10. The method of claim 1, wherein the spent acid fraction is separated into a tar fraction and a de-tarred spent acid fraction by centrifugation.

11. The method of claim 1, wherein the spent acid fraction is separated into a tar fraction and a de-tarred spent acid fraction by liquid-liquid coalescence.

12. The method of claim 1, further comprising fluidizing the tar fraction to provide fluidized tar.

13. The method of claim 12, wherein the tar fraction is fluidized by adding a carrier to the tar fraction.

14. The method of claim 12, wherein the tar fraction is fluidized by adding a surfactant to the tar fraction.

15. The method of claim 12, wherein the tar fraction is fluidized by adding sulfuric acid and a surfactant to the tar fraction.

16. The method of claim 12, further comprising incinerating the fluidized tar to produce sulfur dioxide.

17. The method of claim 16, further comprising oxidizing the sulfur dioxide to produce sulfur trioxide, and contacting the sulfur trioxide with a first sulfuric acid to produce a second sulfuric acid, wherein the second sulfuric acid has a higher sulfuric acid concentration that does the first sulfuric acid.

18. The method of claim 17, further comprising recycling the second sulfuric acid as acid catalyst in the acid-catalyzed chemical reaction.

19. The method of claim 1, further comprising heating the de-tarred spent acid to form concentrated de-tarred sulfuric acid.

20. The method of claim 19, further comprising recycling the concentrated de-tarred sulfuric acid as acid catalyst in the acid-catalyzed chemical reaction.

* * * * *